United States Patent [19]

Rainin

[11] Patent Number: 5,569,279
[45] Date of Patent: Oct. 29, 1996

[54] SURGICAL ABRADING DEVICE

[76] Inventor: Edgar A. Rainin, 111 Wild Oak Ct., Danville, Calif. 94526

[21] Appl. No.: 236,372

[22] Filed: Apr. 29, 1994

[51] Int. Cl.⁶ .................................................. A61B 17/00
[52] U.S. Cl. ................ 606/166; 606/159; 606/1
[58] Field of Search ............................. 604/22; 606/107, 606/159, 161, 170, 166, 131; 128/756–758; 433/125; 451/450, 557

[56] References Cited

U.S. PATENT DOCUMENTS

| 2,489,437 | 11/1949 | Sandoz ..................................... 451/450 |
| 2,491,274 | 12/1949 | McNeill . |
| 3,376,867 | 4/1968 | Kanbar et al. . |
| 3,508,547 | 4/1970 | Deuschle . |
| 3,542,025 | 11/1970 | Gustafson . |
| 4,097,995 | 7/1978 | Danne et al. ............................ 433/125 |
| 4,401,130 | 8/1983 | Halford et al. . |
| 4,834,748 | 5/1989 | McDonald ............................... 606/166 |
| 4,883,454 | 11/1989 | Hamburg . |
| 4,887,994 | 12/1989 | Bedford . |
| 4,990,134 | 2/1991 | Auth . |
| 5,062,796 | 11/1991 | Rosenberg ............................... 433/125 |
| 5,084,005 | 1/1992 | Kachigian . |
| 5,100,424 | 3/1992 | Jang et al. .............................. 606/159 |
| 5,100,425 | 3/1992 | Fischell et al. .......................... 606/159 |
| 5,158,532 | 10/1992 | Peng et al. . |

Primary Examiner—Michael Powell Buiz
Assistant Examiner—William Lewis
Attorney, Agent, or Firm—Bielen, Peterson & Lampe

[57] ABSTRACT

An abrading device for use in surgery such as cataract removal utilizing an element having a resilient body. The element includes an outer surface capable of abrading cellular material from a membrane without damage to the membrane. The element is connected to a guiding implement which may also serve as an irrigator for transporting the abraded material from the eye and for maintaining the shape and integrity of the eye capsule.

19 Claims, 1 Drawing Sheet

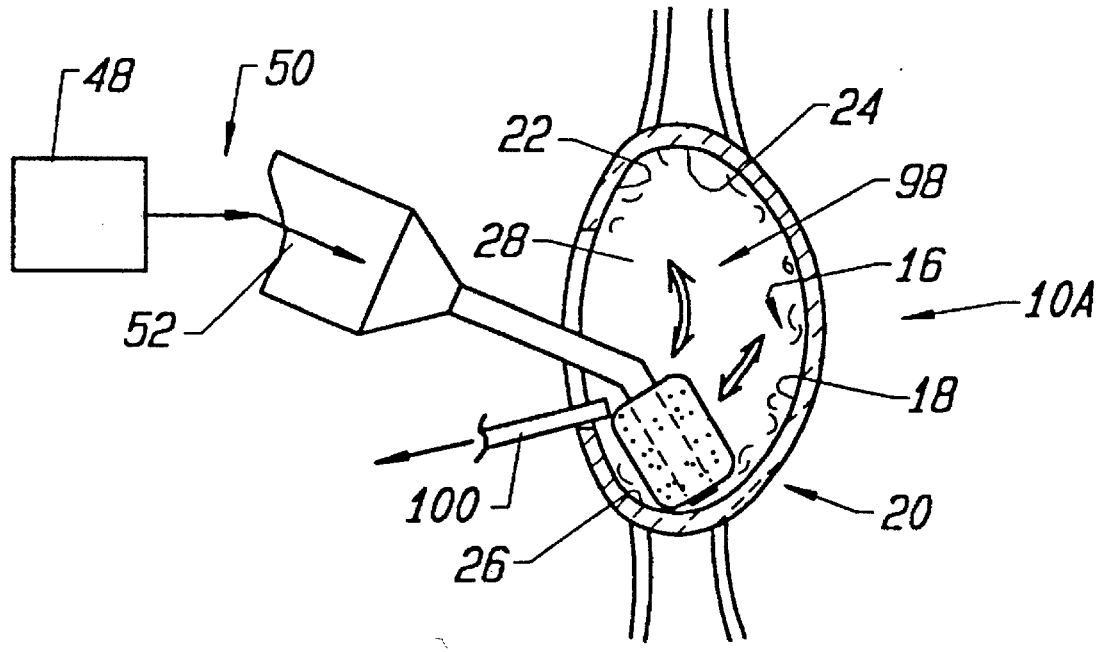

SURGICAL ABRADING DEVICE

BACKGROUND OF THE INVENTION

The present invention involves a novel and useful surgical abrading device which is particularly applicable to eye surgery.

Current surgical techniques for removal of cataracts entail what is termed as extracapsular cataract removal. In such technique, the cataract is removed from the translucent capsule found posteriorly to the iris portion of the eye. In most cases, the posterior, peripheral, and anterior portions of the capsule remain within the eye prior to insertion of an intraocular lens.

A problem arises in this surgical technique when particulate matter, which is usually cellular material, is held in the capsule following cataract removal. Such epithelial cells or opacities, if left behind, tend to grow and spread, which results in the clouding of the normally clear interior or posterior capsular walls. In many cases, a disorganized mass grows in the form of "pearls" which results in a secondary cataract, ie., a clouding of the visual axis.

In the past, the posterior capsule was cut with a fine needle-knife or a laser beam to clear the central optical zone of the shell. Unfortunately, correcting of a secondary cataract condition requires a second surgical procedure, an undesirable step.

U.S. Pat. Nos. 3,542,025, 3,376,867, and 4,401,130 show swab device which are employed in the medical field to absorb fluids.

U.S. Pat. Nos. 2,491,274 and 4,883,459 show swab cleaning devices used topically on the human body.

U.S. Pat. Nos. 3,508,547, 4,887,994, and 5,158,532 describe structures for application swabs.

U.S. Pat. No. 5,084,005 teaches a swab structure including a polymeric foam with grooves for collecting biological samples.

A surgical tool which is capable of clearing the posterior capsule of cellular matter following extra capsular cataract surgery to obviate the need for correcting a secondary cataract condition, would be a notable advance in the surgical field.

SUMMARY OF THE INVENTION

In accordance with the present invention, a novel and useful surgical abrading device and method is herein provided which is particularly useful in cataract surgery.

The present invention is deemed to encompass an element which possesses a resilient body having an outer surface intended for abrading biological material held to a membranous surface. The element may take the form of an open or closed cell foam plastic material with an outer surface that includes a multiplicity of recesses or pocks, which are particularly effective in removing biological material held to a membranous surface. One particular application of the present invention concerns its use in extra capsular cataract surgery. Following removal of the clouded natural lens (a cataract), softer cortical material remains and must be removed to avoid subsequent growth of the same, which can form a secondary cataract.

A relatively rigid implement, which may take the form of an elongated tube, is also employed in the present invention. The relatively rigid implement is capable of being manipulated by the user, which is normally the surgeon in the case of eye surgery. The relatively rigid implement attaches to the element by means for connecting the same to the resilient body of the element. Such connection may take place by any suitable means such as fusion heating, sonic welding, gluing, and the like. When connected, the resilient body may partially or completely surround the relatively rigid implement. In certain cases, the relatively rigid implement may be simply connected to a portion of the outer surface, which is employed for abrading biological material from the membranous surface. In any type of attachment, the connection means permits the outer surface of the resilient body to be available for abrading or scrubbing of biological material from the membranous surface. In addition, the relatively rigid implement may include an angulation which allows the surgeon to reach remote areas of the interior of the lens capsule, in the case of eye surgery. The relatively rigid element may comprise a tube.

Irrigation means may also be found in the present invention for transporting fluid from a fluid source to the tube and through the tube, into the capsule of the eye. In this manner, the capsule is inflated with fluid flowing through the tube during the scrubbing process. Thus, the surgeon is able to scrub the anterior and posterior inner walls of the capsule without danger of the capsule collapsing during this abrading or scrubbing process. The resilient body of the element may include the characteristic of being absorbent to irrigation fluids, although this is not a necessity in the present case. The irrigation means may be attached to the relatively rigid implements and lie adjacent the element during use. For example, the relatively rigid implement may take the form of a forceps having a tubular member attached to one of the legs of the forceps.

The invention may also encompass a method of removing biological material held to a translucent lens capsule found in the eye. In such instance, the surgeon would enter the capsule with the element having a resilient body with an outer surface intended for abrading biological material held to the membranous surface of the lens capsule. As described above, the element would be connected to the relatively rigid implement for this purpose. The surgeon then rubs or abrades the outer surface of the resilient body against the biological material held to the translucent membrane of the capsule until the biological material is free of the membranous surface. The free biological material is then removed by irrigation and/or aspiration devices, or by any other suitable means, from the interior of the capsule. Irrigation is also employed in the method of the present invention to maintain the inflation of the capsule during the abrading process.

Following use of the device of the present invention and the method described above, the lens capsule is suitable for insertion of an intraocular lens to correct aphakia resulting from cataract removal.

It may be apparent that a novel and useful device and method for surgically abrading biological material from a membranous surface has been described.

It is therefore an object of the present invention to provide a surgical abrading device and method which is capable of removing cortical material remaining in a lens capsule in the eye following cataract removal in order to prevent the development of opacities along the surface of the lens capsule.

It is another object of the present invention to provide a surgical abrading device and method which obviates a secondary cataract following cataract surgery due to uninhibited growth of biological material remaining after the removal of the cataract from the lens capsule.

A further object of the present invention is to provide a surgical abrading device and method which is capable of removing harmful biological material from a membranous surface such as a lens capsule of an eye without damaging or harming the membranous surface in any manner.

Yet another object of the present invention is to provide a surgical abrading device and method which may be combined with an irrigation system to maintain inflation of an eye capsule while the device of the present invention is employed.

Another object of the present invention is to provide a surgical abrading device and method which is capable of removing undesirable biological material from the inner surfaces of the lens capsule.

Another object of the present invention is to provide a surgical abrading device and method which is capable of removing invisible and microscopic biological material from the interior of a lens capsule following cataract removal during eye surgery.

The invention possesses other objects and advantages especially as concerns particular characteristics and features thereof which will become apparent as the specification continues.

BRIEF DESCRIPTION OF THE DRAWINGS

FIG. 1 is a side elevational view of the device of the present invention in use within a lens capsule following removal of the cataract, the capsule depicted in section.

FIG. 2 is a side elevational view of the device of the present invention.

FIG. 3 is a sectional view taken along line 3—3 of FIG. 2.

FIG. 4 is a partial side elevational view of a second embodiment of the present invention.

FIG. 5 is a partial side elevational view of a third embodiment of the present invention.

FIG. 6 is a partial side elevational view of a fourth embodiment of the present invention.

FIG. 7 is a partial side elevational view of a fifth embodiment of the present invention.

FIG. 8 is a sectional view taken along line 8—8 of FIG. 7.

FIG. 9 is a front elevational view of a sixth embodiment of the present invention.

For a better understanding of the invention, reference is made to the following detailed description of the embodiments thereof which should be taken in conjunction with the prior described drawings.

DETAILED DESCRIPTION OF THE PREFERRED EMBODIMENTS

Various aspects of the present invention will evolve from the following detailed description of the preferred embodiments thereof which should be taken in conjunction with the prior described drawings.

The invention as a whole is depicted in the drawings by reference character 10 followed by an upper case letter to depict particular embodiments. With reference to FIGS. 1–3, device 10A is shown and includes as one of its portions an element 12. Element 12 possesses a resilient body 14 having an outer surface 16 which is intended for abrading biological material 16 from a membranous surface 18, FIGS. 2 and 3. In the particular application shown in FIG. 1, membranous surface 18 takes the form of the posterior surface of a transparent lens capsule 20 found in an eye. The capsule 20 also includes an anterior inner surface 22. Transparent capsule 20 is generally in the form of an oblate spheroid and further includes fornices 24 and 26. Transparent capsule 20, FIG. 1, is depicted as being in a condition immediately following the removal of a cataract, or clouded natural lens, from the interior 28 of transparent capsule 20. Scrubbing element 12 may be formed of open or closed cell sponge like material. For example, poly vinyl alcohol polymer is suitable for the formation of element 12. Other materials may suffice in this regard also, such as various foam plastic materials, felt, wool, and the like. Element 12 possesses an outer surface 30 having a plurality of recesses or pocks 32 which aid in the scraping process and will be described hereinafter.

Implement 34 is also employed in the present invention. Implement 34 is constructed of a relatively rigid material, when compared to resilient body 14 of element 12. As depicted in embodiment 10A, FIGS. 1–3, implement 34 may take the form of a tube 36 having a first portion 38 and a second portion 40 which are connected to one another at angulation 42. End 44 of second portion 40 extends free of the outer surface 30 of element 12. First portion 38 of tube 36 is formed to a hub 46 which is capable of transporting fluid from a fluid source 48, shown schematically in FIG. 1. Thus, fluid source 48, hub 46, and tube 34 constitute irrigation means 50 for passing fluid from source 48 through end 44 of tube 36. Directional arrow 52 indicates that passage of such fluids, which may be saline solution, air, and the like, through hub 46. Directional arrow 54 indicates the passage of fluid from end 44.

Means 54 is also depicted in the drawings for connecting element 12 to implement 34. Turning to FIG. 3, it may be observed that implement 34 has been fused to element 12. Fused layer 56 is indicated as a thickened line on FIG. 3 for this purpose. Other methods may be employed to connect implement 34 to element 12 such as sonic welding, gluing, and the like. It should be noted that element 12 includes ridges 58 and 60 which form a channel 62 that partially surrounds implement 34.

Turning to FIG. 4, it may be observed that embodiment 10B of the present invention is depicted. Embodiment 10B includes a relatively rigid implement 34 which is attached to the outer surface 64 of scrubbing element 66. End 68 of relatively rigid implement 34 extends outwardly from surface 64. Fusion of implement 34 to scrubbing element 66 forms a shallow channel 70.

Turning now to FIG. 4, it may be observed that embodiment 10C is shown of the present invention. Implement 34 includes end 68 which lies in a shallow channel 72 of resilient scrubbing element 74. Resilient scrubbing element 74 is formed with a rectangular solid end portion 76 in embodiment 10C.

With reference to FIG. 6, it may be seen that embodiment 10D of the present invention is depicted. Resilient scrubbing element 78 includes a lower rounded portion 80 and a diminished cap portion 82 which is heat fused to implement 34.

FIG. 7 illustrates embodiment 10E of the present invention where relatively rigid implement 34 is passed through a resilient scrubbing element 84 and held to the same by heat fusion shown as a thickened portion 86 surrounding implement 34 on FIG. 8. Resilient scrubbing element 84 completely surrounds implement 34 in this case. However, end 68 of implement 34 is still free of resilient scrubbing element 84.

FIG. 9 shows embodiment 10F of the present invention where resilient scrubbing element 88 is held by a relatively rigid implement in the form of forceps 90. Irrigation tube 92 and hub 94 are held to leg 96 of forceps 90 by glue, welding, and the like. It should be noted that hub 94 connects to source of irrigation fluid 48 in a manner similar to that of embodiment 10A of FIG. 1. It should also be seen that resilient scrubbing elements 66, 74, 78, 84, and 88 of embodiments 10B–F may be formed of material similar to resilient element 12 such that the outer surface of each is capable of removing biological material 16 from surfaces 18, 22, and fornices 24 and 26 of capsule 20, in the same manner as embodiment 10A of FIG. 1.

In operation, the user, typically an eye surgeon, inserts device 10A to the interior 28 of capsule 20, FIG. 1. Capsule 20 appears in FIG. 1 in a condition following removal of a cataract during eye surgery. In this regard, various biological cells 16 are held to inner surfaces 18, 22, and fornices 24 and 26. Biological material 16 has been found to include remnants of epithelial cells which may proliferate at a later time if left within interior 28 of capsule 20. Such proliferation may eventually cloud the transparency of capsule 20, requiring secondary cataract removal using a needle-knife or laser cutting device. With reference to FIG. 1, it may be observed that resilient element 12 may be moved back and forth or in a circular motion according to pair of directional arrows 98. Resilient element 12 is located within fornix 26 in FIG. 1 and is able to effect scrubbing in that area through the use of angulation 42 on relatively rigid implement 34. It has been found that resilient element 12 is capable of removing visible and microscopic biological matter during this operation. In additional, element 12 may be pressed vigorously against the interior surfaces 18, 22, and fornices 24 and 26 of capsule 20 without breaking the capsule. Irrigation means 50 may be employed to maintain the inflation of capsule 20 during this procedure. After scrubbing by device 10A, aspiration tube 100 is inserted to capsule 20 to remove biological matter 16 from the interior 28 of capsule 20 following abrasion of the same from capsule 20. Capsule 20 is then available for insertion of an intraocular lens. It has been found that device 10A greatly reduces the need for secondary cataract procedures normally employed in the prior art devices and methods associated with cataract surgery.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A surgical abrading device to remove biological material held to a membranous surface, comprising:
    a. an element including a resilient body having an abrading surface for removing biological material held to a membranous surface, said element including a core of fluid absorbing material;
    b. irrigation means for transporting fluid from a source, said irrigation means including a tubular member; and
    c. connecting means for holding said element to said irrigation means to permit flow of fluid to the membranous surface.

2. The device of claim 1 in which said core comprises a mass of sponge material.

3. A surgical abrading device to remove biological material held to a membranous surface comprising:
    a. an element including a resilient body having an outer abrading surface for removing biological material held to a membranous surface;
    b. irrigation means for transporting fluid from a source, said irrigation means including a tubular member; and
    c. connecting means for holding said element to said irrigation means to permit flow of fluid to the membranous surface, said connecting means including means for connecting said element to said tubular member.

4. The device of claim 3 in which said tubular member is relatively rigid with respect to said element.

5. The device of claim 3 in which said tubular member is at least partially surrounded by said element.

6. The device of claim 5 in which said tubular element includes an open end, said open end of said tubular element being set apart from said outer abrading surface of said element.

7. A surgical abrading device to remove biological material held to a membranous surface comprising:
    a. an element includinq a resilient body having an outer abrading surface for removing biological material held to a membranous surface;
    b. irrigation means for transporting fluid from a source, said irrigation means including a tubular member; and
    c. connecting means for holding said element to said irrigation means to permit flow of fluid to the membranous surface, said connecting means connecting said tubular member to said outer surface of said element.

8. A surgical abrading device to remove biological material held to a membranous surface, comprising:
    a. an element including a resilient body having an outer abrading surface for removing biological material held to a membranous surface;
    b. irrigation means for transporting fluid from a source, said irrigation means including a tubular member;
    c. connecting means for holding said element to said irrigation means to permit flow of fluid to the membranous surface; and
    d. forceps connected to said tubular member.

9. A surgical abrading device to remove biological material held to a membranous surface, comprising:
    a. an element including a resilient body having an outer abrading surface for removing biological material held to a membranous surface;
    b. irrigation means for transporting fluid from a source, said irrigation means including a tubular member; and
    c. connecting means for holding said element to said irrigation means to permit flow of fluid to the membranous surface, said connecting means, includes said element being in surrounding engagement with said tubular member.

10. A surgical abrading device for removing biological material from at least a portion of a translucent capsule found in an eye, comprising:
    a. an element including a resilient body, said element having an outer abrading surface intended for removing biological material held to the face of the translucent capsule;

b. a relatively rigid implement, said implement capable of being manipulated by the user; and c. means for connecting said element to said relatively rigid implement to permit said outer abrading surface of said resilient body of said element to contact the biological material held to the surface of the transparent capsule, said means for connecting said element to said relatively rigid implement further including means from affixing said resilient body in an at least a partially surrounding relationship to said relatively rigid implement.

11. The device of claim 10 which additionally comprises irrigation means for transporting fluid from a source, to said tubular member and through said tubular member.

12. The device of claim 11 in which said tubular member includes an end portion being set apart from said outer surface of said element.

13. A surgical abrading device to removing biological material from at least a portion of a translucent capsule found in an eye;

b. a relatively rigid implement, said implement capable of being manipulated by the user; and c. means for connecting said element to said relatively rigid implement to permit said outer abrading surface of said resilient body of said element to contact the biological material held to the surface of the transparent capsule, said means for connecting said element to said relatively rigid implement further including means for affixing said outer surface of said resilient body to said relatively rigid implement.

14. A surgical abrading device for removing biological material from at least a portion of a translucent capsule found in an eye, comprising:

a. an element including a resilient body, said element having an outer abrading surface intended for removing biological material held to the face of the translucent capsule;

b. a relatively rigid implement, said implement capable of being manipulated by the user, said relatively rigid implement being a tubular member; and c. means for connecting said element to said relatively rigid implement to permit said outer abrading surface of said resilient body of said element to contact the biological material held to the surface of the transparent capsule.

15. A surgical abrading device for removing biological material from at least a portion of a translucent capsule found in an eye, comprising:

a. an element including a resilient body, said element having an outer abrading surface intended for removing biological material held to the face of the translucent capsule;

b. a relatively rigid implement, said implement capable of being manipulated by the user, said relatively rigid implement comprising forceps; and c. means for connecting said element to said relatively rigid implement to permit said outer abrading surface of said resilient body of said element to contact the biological material held to the surface of the transparent capsule.

16. A surgical abrading device for removing biological material from at least a portion of a translucent capsule found in an eye, comprising:

a. an element including a resilient body, said element having an outer abrading surface intended for removing biological material held to the face of the translucent capsule;

b. a relatively rigid implement, said implement capable of being manipulated by the user said relatively rigid implement being an elongated member including an angulation; and c. means for connecting said element to said relatively rigid implement to permit said outer abrading surface of said resilient body of said element to contact the biological material held to the surface of the transparent capsule.

17. A method of removing biological material held to the membranous surface of the translucent lens capsule found in an eye, comprising the steps of:

a. entering the capsule with an element including a resilient body and an outer abrading surface for removing biological material held to the membranous surface, said element being connected to a relatively rigid implement;

b. rubbing the outer surface of the resilient body against the biological material held to the membranous surface to abrade the biological material until the biological material is free of the membranous surface; and c. removing the free biological material from the translucent lens capsule.

18. The method of claim 17 in which said step of entering the capsule with an element further includes said relatively rigid element comprising a tubular member and further comprises irrigating means for delivering fluid to said tubular member and through, said tubular member, and additionally comprises the step of passing fluid to the transparent lens capsule to at least partially inflate said transparent lens capsule.

19. The method of claim 18 which further comprises the step of removing the free biological material from the eye.

\* \* \* \* \*